United States Patent
Jørgensen et al.

(10) Patent No.: US 6,924,133 B1
(45) Date of Patent: Aug. 2, 2005

(54) SPRAY DRIED ENZYME PRODUCT

(75) Inventors: Jørgen Topp Jørgensen, Kalundborg (DK); Carsten Jacobsen, København V (DK); Kim Uhre Hansen, Kalundborg (DK); Anders Jørgensen, Kalundborg (DK); Dan Oftelund, Kalundborg (DK); Poul Bach, Birkerød (DK); Gustav Borup Søndergaard, Hillerød (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/675,950

(22) Filed: Sep. 29, 2000

Related U.S. Application Data

(60) Provisional application No. 60/158,270, filed on Oct. 7, 1999, and provisional application No. 60/185,206, filed on Feb. 25, 2000.

(30) Foreign Application Priority Data

Oct. 1, 1999 (DK) .......................................... 1999 01415
Feb. 17, 2000 (DK) .......................................... 2000 00251

(51) Int. Cl.$^7$ .............................. A61K 9/14; A61K 9/16
(52) U.S. Cl. ....................................... 435/187; 435/183
(58) Field of Search ................................ 435/187, 183

(56) References Cited

U.S. PATENT DOCUMENTS

| | | | | |
|---|---|---|---|---|
| 4,233,405 A | * | 11/1980 | Neubeck | 453/187 |
| 4,294,930 A | * | 10/1981 | Barach et al. | 435/261 |
| 6,146,879 A | * | 11/2000 | Liddell et al. | 435/260 |

FOREIGN PATENT DOCUMENTS

| | | | |
|---|---|---|---|
| EP | 0 366 303 A2 | | 10/1989 |
| GB | 1483591 | * | 8/1977 |
| WO | WO-91/06638 A1 | * | 5/1991 |
| WO | 91/06638 | * | 5/1991 |
| WO | 93/07260 | * | 4/1993 |

\* cited by examiner

*Primary Examiner*—Jean C. Witz
(74) *Attorney, Agent, or Firm*—Elias Lambiris; Jason Garbell

(57) ABSTRACT

The invention relates to a particle comprising an enzyme and a biomass, to a process for preparing a particle comprising spray drying an enzyme and biomass containing fermentation broth starting material, to obtain a solid particle comprising an enzyme and a biomass and to a process for preparing an enzyme containing particle comprising spray drying an aqueous enzyme containing liquid starting material to obtain a spray dried first enzyme containing particle and subsequently subjecting the first dry particle to a process selected from granulation and coating and combinations thereof to obtain a second dry enzyme containing particle.

16 Claims, No Drawings

SPRAY DRIED ENZYME PRODUCT

CROSS-REFERENCE TO RELATED APPLICATIONS

This application claims priority under 35 U.S.C. 119 of Provisional applications 60/158,270 and 60/185,206 filed Oct. 7, 1999 and Feb. 25, 2000 and of Danish applications PA 2000 01415 and PA 2000 00251 filed Oct. 1, 1999 and Feb. 17, 2000, the contents of which are fully incorporated herein by reference.

TECHNICAL FIELD

This invention relates to enzyme containing particles, to processes for preparing enzyme containing particles, and to the use of enzyme containing particles in compositions and applications of such particles and compositions.

BACKGROUND OF THE INVENTION

Enzyme products are known and used in a variety of industries and applications.

Known art for providing dry particulate enzyme products includes:

Spray dried products, as described in Michael S. Showell (editor); *Powdered detergents*; Surfactant Science Series; 1998; vol. 71; page 140–142; Marcel Dekker and GB 1,360,969.

Layered products, as described in WO 97/23606 and U.S. Pat. No. 5,814,501

Improved properties of biological compounds such as enzymes, desired or required by industry and applications has led to development of complex particulate enzyme products, a task in which many challenging problems arise. The products should be cheap with respect to processes and process components and chemicals but should also provide the enzyme product with desired properties such as improved enzyme storage stability, lowered dusting characteristics, improved particle mechanical strength, desired color, shape and size.

SUMMARY OF THE INVENTION

The invention concerns a first aspect a process for preparing a particle comprising spray drying a fermentation broth starting material comprising an enzyme and a biomass, to obtain a solid particle comprising an enzyme and a biomass.

In a second aspect, the invention provides a process for preparing an enzyme containing particle comprising spray drying an aqueous enzyme containing liquid starting material to obtain a spray dried first enzyme containing particle and subsequently subjecting the first dry particle to a process selected from granulation and coating and combinations thereof to obtain a second dry enzyme containing particle.

In additional aspects, the invention also provides particles comprising an enzyme and a biomass, compositions comprising such particles and methods of using such particles and compositions.

The present invention provides simple and cost effective processes for producing dry enzyme particles having good properties.

DEFINITIONS

The term "fermentation broth" as used in the context of the present invention is to be understood as an aqueous composition, comprising both an enzyme and the microbial cells and/or cell debris thereof, which during a fermentation process has produced the enzyme.

The term "cell debris" as used in the context of the present invention is to be understood as un-dissolved parts of the fermented microbial cells including construction extending from the cell, such as mycelium form fungal cells.

The term "biomass" as used in the context of the present invention is to be understood as synonym for microbial cells, cell debris or a combination thereof.

The term "fermentation filtrate" as used in the context of the present invention is to be understood as a fermentation broth from which microbial cells and cell debris has been removed.

The term "enzyme concentrate" as used in the context of the present invention is to be understood as a fermentation filtrate which has been processed to increase the concentration of enzyme.

The term "SPAN" as used in the context of the present invention is to be understood as the width of the particle size distribution (PSD) and is expressed as:

$$SPAN = (D90 - D10)/D50.$$

The PSD can be expressed in terms of the mass mean diameter of the individual particles. A mean mass diameter of D50 is the diameter at which 50% of the granules, by mass, have a smaller diameter, while 50% by mass have a larger diameter. The values D10 and D90 are the diameters at which 10% and 90%, respectively, of the granules, by mass, have a smaller diameter than the value in question.

The term "Rayleigh Atomizer" is to be understood as an atomizer capable of producing droplets of liquid having a low SPAN value (usually SPAN values below 1.5 can be obtained such as between 0.9–1.3), said atomizer characterized by comprising a spraying member and a surface member comprising at least one bore hole. In a preferred embodiment the Rayleigh Atomizer is a rotating atomizing device wherein a liquid is atomized by distributing the liquid onto the inner surface of a rotating hollow cylinder comprising bore holes, the liquid forming droplets by passing the cylinder wall through the bore holes. Such an atomizer is described in WO 94/21383 claims 9–30 and FIGS. 1–18 and methods for atomizing in claims 1–8 all incorporated herein by reference.

DETAILED DESCRIPTION OF THE INVENTION

Microorganisms

The microbial cells or micro-organisms, which is fermented to produce a fermentation broth comprising an enzyme and a biomass may be any micro-organism suitable for fermentation.

The micro-organism a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial micro-organism is a *Bacillus lentus, Bacillus licheniformis, Bacillus clausii, Bacillus stearothermophilus,* or *Bacillus subtilis* cell. In another preferred embodiment, the *Bacillus* cell is an alkalophilic *Bacillus*.

The micro-organism may also be an eukaryote, such as a mammalian, insect, plant, or fungal cell. In a preferred embodiment, the micro-organism is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal micro-organism is a yeast cell. "Yeast" as used herein includes ascosporogenous yeast (Endomycetales), basidiosporogenous yeast, and yeast belonging to the Fungi Imperfecti (*Blastomycetes*). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium* Series No. 9, 1980).

In an even more preferred embodiment, the yeast microorganism is a *Candida, Hansenula, Kluyveromyces, Pichia, Saccharomyces, Schizosaccharomyces*, or *Yarrowia* cell.

In a most preferred embodiment, the yeast microorganism is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast micro-organism is a *Kluyveromyces lactis* cell. In another most preferred embodiment, the yeast micro-organism is a *Yarrowia lipolytica* cell.

In another more preferred embodiment, the fungal microorganism is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal micro-organism is a cell of a species of, but not limited to, *Acremonium, Aspergillus, Fusarium, Humicola, Mucor, Myceliophthora, Neurospora, Penicillium, Thielavia, Tolypocladium* or *Trichoderma*.

In a most preferred embodiment, the filamentous fungal micro-organism is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal micro-organism is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell.

In another most preferred embodiment, the filamentous fungal micro-organism is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

The present invention also encompasses variants of the above mentioned microorganisms resulting from altering the genetic material of said microorganism by conventional gene manipulation methods, such inserting foreign nucleotide sequences encoding an enzyme into said microorganisms.

The Enzyme

The enzyme in the context of the present invention may be any enzyme or combination of different enzymes obtainable by fermentation. Accordingly, when reference is made to "an enzyme" this will in general be understood to include both a single enzyme and a combination of more than one enzyme.

It is to be understood that enzyme variants (produced, for example, by recombinant techniques) are included within the meaning of the term "enzyme". Examples of such enzyme variants are disclosed, e.g., in EP 251,446 (Genencor), WO 91/00345 (Novo Nordisk), EP 525,610 (Solvay) and WO 94/02618 (Gist-Brocades NV). The enzyme classification employed in the present specification and claims is in accordance with *Recommendations* (1992) *of the Nomenclature Committee of the International Union of Biochemistry and Molecular Biology*, Academic Press, Inc., 1992.

Accordingly the types of enzymes which may appropriately be incorporated in the enzyme product of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1) such as haloperoxidase, laccases (EC 1.10.3.2) and glucose oxidases (EC 1.1.3.4)], while preferred transferases are transferases in any of the following sub-classes:

a) Transferases transferring one-carbon groups (EC 2.1);
b) Transferases transferring aldehyde or ketone residues (EC 2.2); acyltransferases (EC 2.3);
c) Glycosyltransferases (EC 2.4);
d) Transferases transferring alkyl or aryl groups, other than methyl groups (EC 2.5); and
e) Transferases transferring nitrogenous groups (EC 2.6).

A most preferred type of transferase in the context of the invention is a transglutaminase (protein-glutamine γ-glutamyltransferase; EC 2.3.2.13).

Further examples of suitable transglutaminases are described in WO 96/06931 (Novo Nordisk A/S).

Preferred hydrolases in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases].

In the present context, the term "carbohydrase" is used to denote not only enzymes capable of breaking down carbohydrate chains (e.g. starches) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses):

α-amylases (3.2.1.1), β-amylases (3.2.1.2), glucan 1,4-α-glucosidases (3.2.1.3), cellulases (3.2.1.4), endo-1,3(4)-β-glucanases (3.2.1.6), endo-1,4-β-xylanases (3.2.1.8), dextranases (3.2.1.11), chitinases (3.2.1.14), polygalacturonases (3.2.1.15), lysozymes (3.2.1.17), β-glucosidases (3.2.1.21), α-galactosidases (3.2.1.22), β-galactosidases (3.2.1.23), amylo-1,6-glucosidases (3.2.1.33), xylan 1,4-β-xylosidases (3.2.1.37), glucan endo-1,3-β-D-glucosidases (3.2.1.39), α-dextrin endo-1,6-α-glucosidases (3.2.1.41), sucrose α-glucosidases (3.2.1.48), glucan endo-1,3-α-glucosidases (3.2.1.59), glucan 1,4-β-glucosidases (3.2.1.74), glucan endo-1,6-β-glucosidases (3.2.1.75), arabinan endo-1,5-α-L-arabinosidases (3.2.1.99), lactases (3.2.1.108), chitosanases (3.2.1.132) and xylose isomerases (5.3.1.5).

Examples of commercially available oxidoreductases (EC 1.-.-.-) include Gluzyme™ (enzyme available from Novo Nordisk A/S).

Examples of commercially available proteases (peptidases) include Kannase™, Everlase™, Esperase™, Alcalase™, Neutrase™, Durazym™, Savinase™, Pyrase™, Pancreatic Trypsin NOVO (PTN), Bio-Feed™ Pro and Clear-Lens™ Pro (all available from Novo Nordisk A/S, Bagsvaerd, Denmark).

Other commercially available proteases include Maxatase™, Maxacal™, Maxapem™, Opticlean™ and Purafect™ (available from Genencor International Inc. or Gist-Brocades).

Examples of commercially available lipases include Lipoprime™ Lipolase™, Lipolase™ Ultra, Lipozyme™, Palatase™, Novozym™ 435 and Lecitase™ (all available from Novo Nordisk A/S). Other commercially available lipases include Lumafast™ (*Pseudomonas mendocina* lipase from Genencor International Inc.); Lipomax™ (*Ps. pseudoalcaligenes* lipase from Gist-Brocades/Genencor Int. Inc.; and *Bacillus* sp. lipase from Solvay enzymes.

Examples of commercially available carbohydrases include Alpha-Gal™, Bio-Feed™ Alpha, Bio-Feed™ Beta, Bio-Feed™ Plus, Bio-Feed™ Plus, Novozyme™ 188, Celluclast™, Cellusoft™, Ceremyl™, Citrozym™, Denimax™, Dezymer™, Dextrozyme™, Finizym™, Fungamyl™, Gamanase™, Glucanex™, Lactozym™, Maltogenase™, Pentopan™, Pectinex™, Promozyme™, Pulpzyme™, Novamyl™, Termamyl™, AMG™ (Amyloglucosidase Novo), Maltogenase™, Sweetzyme™ and Aquazym™ (all available from Novo Nordisk A/S).

Combinations of enzymes may be obtained by fermenting two or more enzymes simultaneously in the same fermentation broth using this liquid or a processed liquid thereof as a starting material in a process of the invention. Alternatively combinations of enzymes may be obtained by fermenting the enzymes separately and using mixtures of different fermentation broths and/or processed liquids thereof as a starting material for the process of the invention.

Fermentation Broths and Enzyme Containing Liquids

The starting material for processes of the invention is a fermentation broth or an enzyme containing liquid depending on the steps of the process.

In the first aspect of the invention, supra, the starting material is a fermentation broth and the process comprises the step of spray drying said fermentation broth. As defined herein a fermentation broth in accordance with the invention comprises microbial cells and/or cell debris thereof (biomass). Some of is the biomass may be removed before spray drying to optimize the broth properties and suitability for spray drying, e.g. to adjust viscosity. However, the more biomass is removed the more expensive the process will be. Accordingly, in a preferred embodiment the fermentation broth comprises at least 10% of the biomass, more preferably at least 50%, even more preferably at least 75% and most preferably at least 90% or at least 95% of the biomass originating from the fermentation. In another preferred embodiment the broth contains 0–31% w/w dry matter, preferably 0–20% w/w, more preferably 0–15% w/w such as 10–15% w/w dry matter, 0% dry matter being excluded from said ranges. The biomass may constitute up to 90% w/w of the dry matter, preferably up to 75% w/w, more preferably up to 50% w/w of the dry matter, while the enzyme may constitute up to 50% w/w of the dry matter, preferably up to 25% w/w, more preferably up to 10% w/w of the dry matter.

In another preferred embodiment of the first aspect of the invention, coarse particles or bodies such as straw, rubble, soy grits and other non-biomass insolubles are removed from the fermentation broth starting material before spray drying. Such coarse particles or bodies may originate from additives such nutrients added during fermentation. The coarse particles or bodies may be removed by straining, sedimentation, centrifugation and/or decanting the broth. This process is called de-sludging.

In the second aspect of the invention the starting material is an enzyme containing liquid and the process comprises the step of spray drying said enzyme containing liquid to obtain a first dry enzyme containing particle and subsequently subjecting the first dry particle to a second process step to obtain a second dry enzyme containing particle.

The starting material to be dried in accordance with the second aspect of the invention, is preferably an aqueous liquid, such as an aqueous solution or dispersion of one or more enzymes.

In a preferred embodiment of the second aspect of the invention, the starting material is a fermentation broth or a fermentation broth, which have been subjected to one or more processing steps, such as a fermentation filtrate or an enzyme concentrate as defined, supra.

Removing the biomass from a fermentation broth to provide a fermentation filtrate may be achieved by known methods such as filtration, centrifugation, flocculation and combinations thereof.

An enzyme concentrate may be provided for by processing a fermentation filtrate. Such processing includes evaporation of solvents (e.g. water), ultra filtration to reduce contents of water and low molecular components, extraction of enzyme from the fermentation filtrate into a second liquid. Also purification through column chromatography may be used, e.g. by pumping the fermentation filtrate through a column comprising a resin, allowing the enzyme to pass at a slower or faster rate than water, salts or other constituents of the filtrate.

In both first and second aspect of the invention the starting material may, before spray drying, be added material which will improve the properties of the resulting dry enzyme containing powder or products resulting here from. Useful additives includes materials selected from salts, inorganic minerals or clays, carbohydrates, coloring pigments, cellulose or derivatives thereof, biocides, dispersants, anti foaming agents, viscosity regulating agents, acid agents, alkaline agents, enzyme stabilizers, enzyme inhibitors, binders other enzymes and combinations thereof. Addition of inorganic salts such as alkali and earth alkali salts chloride, sulfate, nitrate and carbonate, e.g. Calcium salts may activate the enzyme. Other salts, especially sodium sulfate or chloride may be used as a filler material. Addition of carbohydrates such as sucrose and/or starch may add to particle strength and improve enzyme stability. Addition of coloring pigments such as titanium dioxide may provide the broth and the finished particulate enzyme product with a desired color. Addition of cellulose may provide strength and elasticity to the enzyme particles. Addition of stabilizers such as methionin or thiosulphate may provide protection of the enzyme so, that it is less liable to inactivation during processes of the invention and storage of the obtained enzyme products. Addition of minerals and clays such as zeolites, kaolin, bentonite, talc's, and/or silicates may provide increased compactness of the dried enzyme particles and granules there from. Addition of inhibitors such as boric acid protease inhibitors may improve process yields by lowering protease digestion of the enzyme or self digestion. Addition of biocides such as Rodalon® enables control of the microbial stability and may reduce odour of the final product. Addition of acids or bases may be used to control pH to a desired level.

Also in both first and second aspect of the invention the starting material may, before spray drying, be subjected to physical treatments such heating and/or cooling and/or radiating the broth as well as mixing, aeration, or ultra-sound treatment.

In an important embodiment of the invention is that the starting material, before spray drying, preferably is treated to kill living microbial cells or treated to hydrolyze or disintegrate remaining genetic material such as DNA (genomic or plasmidic) or other poly-nucleotides present in the broth or liquid.

Sterilization of a broth in the context of the first aspect of the invention may be achieved by addition of a biocide such as Rodalon® (Benzalkonium chloride), heating (pasteurization) or radiation. Sterilization of a fermentation filtrate or enzyme concentrate broth in the context of the second aspect of the invention may be achieved by the same means as for a broth or it may be achieved by sterile filtration. In all cases disintegration of genetic material may be achieved using known methods, such as enzymatic digestion of poly-nucleotides.

For many applications useful enzyme-containing particles requires that the particles contains a certain minimum amount of active enzyme. Accordingly, in a preferred embodiment the starting material should contain a certain minimum concentration of enzyme in the liquid and/or the enzyme should constitute a certain minimum percentage of the solids (i.e. non-volatile components) in the liquid in order to produce particles by the process of the invention, which have a useful enzyme contents. We have surprisingly found it possible to provide fermentations which directly yields fermentation broths having a sufficiently high enzyme content, so that the broth may be dried directly or only minimally refined by removing biomass, sterilization and addition of additives to obtain a dry powder having a an enzyme content sufficiently high to give an enzyme product useful in most applications. Preferably the enzyme content in the fermentation broth or fermentation filtrate before subjecting it to any further refinement processes is at least 3 mg active enzyme protein per liter liquid phase of the fermentation broth, more preferably at least 20 mg/l, more preferably at least 50 mg/l, most preferably at least 75 mg/l, such as 80 mg/l or more.

The starting material for the process of the invention should further have a viscosity suitable for pumping the liquid, preferably in the range 5–5000 cps.

Drying Processes

Drying of a broth, filtrate or concentrate, in accordance with the invention is achieved by a spray drying process, comprising transporting the broth, filtrate or concentrate through an atomizing device into a drying chamber wherein droplets of atomized broth, filtrate or concentrate is mixed with a stream of air in which the volatile parts of the droplets are evaporated and removed leaving dried enzyme-containing particles.

In a preferred embodiment of the invention the broth, filtrate or concentrate is transported by means of a pumping device and is preferably preheated to a temperature between 5–150° C., preferably between 50–120° C., more preferably between 90–110° C.

The atomization device may suitably be selected from high speed rotating disk atomizers, pressure nozzle atomizers, pneumatic nozzle atomizers or sonic nozzle atomizers such as described in the Course Material from the Microencapsulation Seminar, held by Center for professional advancement on May 9 to May 11, 1990 in Amsterdam.

However, a preferred special atomizer, which in use produces a superior dried enzyme containing particle is a Rayleigh atomizer with which improved properties of the is particles can be obtained, such as increased mechanical strength, lower dusting, narrow particle size distribution, i.e. a low SPAN value and improved spherical shape may be obtained. One such atomizer is described in WO 94/21383, which is hereby incorporated by reference.

The spray dried powder which usually will have a water content of 10–15% by weight may preferably be further dried to an even lower moisture contents such as below about 5% w/w by introducing the spray dried particles into a fluid bed drying device in which the spray dried particles is kept fluidized by an upwards stream of preferably heated and dried air evaporating excess moisture from the fluidized particles.

The properties of the obtained spray dried solid enzyme containing particles will depend on the spray drying conditions and additives added to the starting material. In some spray drying processes very small particles are formed initially in the drying step which subsequently agglomerate or glue together to form larger somewhat fragile agglomerates in the end of the spray drying process. Such agglomerated particles may preferably have a mean diameter or size in the range of 150–2000 $\mu$m. In other spray drying processes, such as using the atomizing device of WO 94/21383 smaller non-agglomerated more homogeneous particles may be produced because of the special design of the atomizer. Such particles generally have better dusting, strength and SPAN properties and the mean size preferably fall within the range of 50–300 $\mu$m, more preferable within 100–200 $\mu$m.

Preferred spray drying processes are processes which yields product have a narrow size distribution, i.e. a low SPAN value. Preferably the SPAN value is below about 2.5, more preferably below about 2.0, more preferably below about 1.5, and most preferably below about 1.0.

Processing of Dried Particles

The process of the second aspect of the invention (supra) requires that the first spray dried particles are subsequently subjected to a process selected from granulation and coating and combinations thereof to obtain a second dry enzyme containing particle. Granulation processes includes mixer granulation, prilling, extrusion, fluid bed and compacting processes.

The present invention, however, also encompasses processes, wherein particles obtained from spray drying a fermentation broth are subsequently subjected to a process selected from granulation and coating and combinations thereof.

Such further processing improves the properties of the enzyme containing particles.

Mixer Granulation

A mixer granulation process includes mixing the spray dried enzyme-containing particles with water and components selected from binders, fibers, salts, water insoluble minerals, pigments, enzyme stabilizers or combinations thereof. The water is added in sufficient amounts to agglomerate the solid components into granules of a desired mean size.

Binders include binders with a high melting point or no melting point at all and of a non waxy nature e.g. polyvinyl pyrrolidon, dextrins, polyvinylalkohol, cellulose derivatives, for example hydroxypropyl cellulose, methyl cellulose or CMC. A suitable binder is a carbohydrate binder such as Glucidex 21D available from Roquette Freres, France.

Fibers include pure and/or or impure cellulose in fibrous form such as sawdust, pure fibrous cellulose, cotton, or other forms of pure or impure fibrous cellulose. Also, filter aids based on fibrous cellulose can be used. Several brands of cellulose in fibrous form are on the market, e.g. CEPO and ARBOCELL. In a publication from Svenska Tr ämjolsfabrikerna AB, "Cepo Cellulose Powder" it is stated that for Cepo S/20 cellulose the approximate maximum fiber length is 500 $\mu$m, the approximate average fibre length is 160 $\mu$m, the approximate maximum fibre width is 50 $\mu$m and the approximate average fibre width is 30 $\mu$m. Also, it is stated that CEPO SS/200 cellulose has an approximate maximum fibre length of 150 $\mu$m, an approximate average fibre length of 50 $\mu$m, an approximate maximum fiber width of 45 $\mu$m and an approximate average fiber width of 25 $\mu$m. Cellulose fibers with these dimensions are very well suited for the purpose of the invention. The words "Cepo" and "Arbocel" are Trade marks. A preferred fibrous cellulose is Arbocel™ BFC200. Also synthetic fibres may be used as described in EP 304331 B1 and typical fibres may be made of polyethylene, polypropylene, polyester, especially nylon, polyvinylformat, poly(meth)acrylic compounds.

Salts include water soluble and/or insoluble salts such as alkali and/or earth alkali salts of sulfate, chloride, carbonate and phosphate.

Water insoluble minerals include zeolites, clays like kaolin and bentonite, talcs, and/or silicates.

Pigments include titaniumdioxide.

Enzyme stabilizers include alkaline or neutral materials, reducing agents, antioxidants and/or salts of first transition series metal ions. Each of these may be used in conjunction with other protective agents of the same or different categories. Examples of alkaline stabilizers agents are alkali is metal silicates, -carbonates or bicarbonates which provide a chemical scavenging effect by actively neutralizing e.g. oxidants. Examples of reducing protective agents are salts of sulfite, thiosulfite or thiosulfate, while examples of antioxidants are methionine, butylated hydroxytoluene (BHT) or butylated hydroxyanisol (BHA). Most preferred agents are salts of thiosulfates, e.g. sodium thiosulfate. Mixer granulation processes are known to the art e.g. from U.S. Pat. No. 4,106,991 (NOVO NORDISK) and related documents EP 170360 B1 (NOVO NORDISK), EP 304332 B1 (NOVO NORDISK), EP 304331 (NOVO NORDISK), WO 90/09440 (NOVO NORDISK) and WO 90/09428 (NOVO NORDISK) in which the addition of a liquid enzyme concentrate in the context of this invention is replaced by addition of water to the spray dried enzyme containing particles. Mixer granulation processes also includes so called "marumerizer" processes as described in U.S. Pat. No. 4,661,452 incorporated by reference.

In a preferred embodiment the enzyme containing mixture to be processed in a mixer granulation process may also comprise a particulate component having a diameter less than the diameter of the finished granule. By adding such a particulate component to the process the size and/or size distribution may be better controlled as described in Danish patent application PA 1999 01000 (unpublished at the filing date of the present application) hereby incorporated by reference. The particulate component may be an agglomerate made from inorganic or organic starting materials which are capable of maintaining the particulate integrity (i.e. it does not disintegrate during the mixer granulation process). An inorganic particulate component may be e.g. an agglomerated silica and/or salt. An organic particulate compound may be a natural compound such as agglomerated carbohydrates, e.g. sugars, starches dextrins or it may be an agglomerated artificial compound or polymeric compound. A preferred particulate compound is however a vegetable flour. The term "vegetable flour" here encompasses, within the scope of the invention, all powdered grained products, which have been obtained by size reduction (grinding) of solid vegetable materials of natural origin (the flour source). It is expedient in the method according to the invention to use vegetable flours that are obtained by grinding of cereal grains, legumes and/or fruits of the *Malvateae* family (e.g., cottonseed). The cereals that can serve as flour sources within the scope of the invention are especially wheat or rye, but barley, oats, rice, and maize, as well as sorghum and other types of millet can also be used. Although buckwheat itself is not a cereal (it is a knot grass), its beechnut-like flour-yielding parts can likewise be used as flour source within the scope of the invention. In a particular variation of the invention legumes may serve as a flour source. Legumes here are to be understood as vegetable foodstuffs (legumes) belonging to the fruits and vegetables. The fruits of *leguminous* species such as *Pisum* (pea), *Cajamus* (pigeon pea), *Cicer* (chick pea); *lens* (lentils); *Phaseolus* (kidney bean), *Vigna* (cow pea); *Dolchius* (lablab bean); *Cassavalia* (sword bean), *Vicia* (horse-bean or vetch); *Peluschken* [maple peal; *Arachis* (peanut); lupins; lucerne; soybeans as well as lima beans and, if applicable, other legumes and other *Malvaceae* fruits (e.g., of the genus *Gossipium*, cotton); potato or yams may be considered as flour sources within the scope of the invention. Especially preferred are peas and in particular soybeans. The particulate compound of the invention may also be a combination of the above mentioned flours and/or agglomerates. A preferred particulate compound is a wheat based flour such the commercially available product Farigel (Farigel de Ble F1100, WestHove, France). The vegetable flour of the invention has preferably been subjected to a steam treatment e.g. with dry superheated steam with a temperature of about 100° C. to about 110° C. at nearly normal pressure to low over pressure (e.g., 0.8 to 1.2 bar over pressure) and a treatment time (residence time in the superheated steam treatment apparatus described below) of up to about 1 hour. Dry superheated steam is a superheated and unsaturated steam, which can be obtained in the conventional way by superheating and removal of possible water condensate or by expansion of steam from high pressure. The particulate component of the invention is distinguished by the steam treatment being done after grinding the vegetable flour source, ie. on the prepared particulate component ready to be used in the mixer granulation process. The advantages of using a steam treated particulate component is of course that that it lowers the number of bacteria or fungus present in the particulate component which may cause microbial growth in the product, but more important the particulate component will be fully or partly gelatinised. Gelatinising improves the integrity of the particles so they do not disintegrate, dissolves or becomes dispersed in the granulation process, but keep their particulate characteristics.

The preferred mean particle size of the particulate component is at least 40 μm, more preferred at least 60 μm such as at least 80 μm, e.g. at least 100 μm. Some useful particulate components may be even larger e.g. have a mean particle size of at least 140 μm or even at least 200 μm.

The mixing equipment can be a batch mixer or a continuous mixer, such as a convective mixer [see, e.g., Harnby et al., *Mixing in the Process Industries*, pp. 39–53 (ISBN 0-408-11574-2)]. Non-convective mixing equipment, e.g. rotating drum mixers or so-called pan-granulators, may also be employed.

Prilling Process

In a prilling process the spray dried enzyme particles is suspended in molten wax and the suspension is spray cooled, e.g. through an atomizing device, into a cooling chamber where the droplets wax comprising enzyme particles solidify. This process is known from Michael S. Showell (editor); *Powdered detergents*; Surfactant Science Series; 1998; vol. 71; page 140–142; Marcel Dekker and DK-PA 1999 01358 both hereby incorporated by reference. The atomizer used in the prilling process is suitably the same as described for spray drying, supra, preferably a Rayleigh atomiser.

Prilled particles may be made to have a desired mean size and a uniform density and further the enzyme is protected within the wax matrix. The term "wax" as used herein, is to be construed as a compound having a melting point between 25–150° C. Preferred waxes are organic compounds or salts of organic compounds having a melting point in the said range or mixtures thereof. By applying mixtures of different waxes, optionally in combination with heavy and/or light solids, enzyme particles of a desired true density can be obtained. Also, an important feature of the wax or mixture of waxes is that the wax should be water soluble or water dispersible, preferably in neutral and alkaline solution, so that the wax matrix of the enzyme particle may disintegrate and/or dissolve in an aqueous solution. Examples of water soluble waxes are poly ethylene glycols (PEG's) Accordingly amongst water soluble waxes the solubility of wax in water should preferably be up to 75 parts wax to 25 parts water, such as for PEG 1000. Amongst water insoluble waxes which are dispersible in an aqueous solution are triglycerides and oils. Further a useful wax do not dissolve or disintegrate in a substantially nonaqueous liquid phase. The term "substantially nonaqueous" in this context may be defined as the liquid phase containing little (e.g. below 5% w/w or below 3% w/w) or no water (non-aqueous). The wax should also be compatible with the enzyme, i.e. it should not inactivate the enzyme, e.g. by reacting with the enzyme or permanently altering structures, such as foldings, helical portions, sheeted portions, prosthetic groups and the like necessary for the enzyme to retain the activity. Still further the wax should be mixable with the enzyme, i.e. the enzyme may be dissolved in the (molten) wax and/or the enzyme may be dispersed in the (molten) wax in an amorphous or crystalline form as enzyme protein particles. A suitable wax is in a solid state at room temperature (25° C.), and accordingly is has a melting point or a melting range (polymer waxes tend to melt over a range of temperatures) above this temperature. A preferred wax has a melting point or range between about 35° C. to about 120° C. The lower limit is preferred to set a reasonable distance between the temperature at which the wax melts to the temperature at which liquid detergents comprising the enzyme particles are usually stored (20–30° C.). Also, difficulties is contemplated, in the manufacture of the enzyme particles when the melting point of the wax is below 35° C. The upper temperature limit is set as the maximum temperature usually applicable for enzymes without experiencing significant losses of enzyme activity, due to heat denaturation. A more preferred melting point or range is between about 40° C. to about 100° C., such as between about 50° C. to about 80° C. In a further preferred embodiment the wax have a molecular weight between about 150 Daltons to about 10.000 Daltons. The wax may be chemically synthesized or it may equally well be a wax isolated from a natural source or a derivative thereof. Accordingly in the wax of the invention is preferably selected from the following non limiting list of waxes.

Poly ethylene glycols, abbreviated PEG, type of wax. Different PEG waxes are commercially available having different molecular sizes, wherein PEG's with low molecular sizes also have the lowest melting points. Examples of suitable PEG's are PEG 1500, PEG 3000, PEG 4000, PEG 6000, PEG 9000 e.g. from BASF—Germany. To meet the desired properties of true density and melting point for the wax and/or the enzyme particle, it also contemplated that mixtures of waxes with low melting point with waxes of a high melting point is a very useful embodiment of the invention.

polypropylens or polyethylens or mixtures thereof.

Nonionic tensides which are solid at room temperature such as ethoxylated fatty alcohols having a high level of ethoxy groups such as Lutensol AT80 from BASF having 80 units of ehtyleneoxide per molecule. Alternatively polymers of ethyleneoxide, propyleneoxide or copolymers thereof are useful, such as in block polymers, e.g. Pluronic PE 6800 from BASF Germany.

Waxes isolated from a natural source, such as Carnauba wax (melting point between 80–88° C.), Candelilla wax (melting point between 68–70° C.) and bees wax. Other natural waxes or derivatives thereof are waxes derived from animals or plants, e.g. of marine origin. Examples of such waxes are hydrogenated ox tallow, hydrogenated palm oil, hydrogenated cotton seeds and/or hydrogenated soy bean oil, wherein the term "hydrogenated" as used herein is to be construed as saturation of unsaturated carbohydrate chains, e.g. in triglycerides, wherein carbon=carbon double bonds are converted to carbon—carbon single bonds. An example hydrogenated palm oil is commercially available e.g. from Hobum Oele und Fette GmbH—Germany or Deutche Cargill GmbH—Germany.

Fatty acid alcohols, such as the linear long chain fatty acid alcohol NAFOL 1822 ($C_{18,20,22}$) from Condea Chemie GMBH —Germany, having a melting point between 55–60° C. and having a true density of about 0.96 g/cm$^3$.

Mono-glycerider and/or di-glycerider, such as glyceryl stearate, wherein stearate is a mixture of stearic and palmitic acid are useful waxes. An example of this is Dimodan PM—from Danisco Ingredients, Denmark—having a melting point of about 1 g/cm$^3$ Fatty acids, such as hydrogenated linear long chained fatty acids.

Paraffines, i.e. solid hydrocarbons.

Micro-crystalline wax.

In further embodiments waxes which are useful in the invention can be found in C. M. McTaggart et. al., Int. J. Pharm. 19, 139 (1984) or Flanders et.al., Drug Dev. Ind. Pharm. 13, 1001 (1987) both incorporated herein by reference.

Extrusion Processes

In an extrusion or pelletizing process moisture is added to the spray dried enzyme containing particles, either alone or mixed with additive such as described for mixer granulation, to provide an enzyme containing paste. This paste is then pressed to pellets or under pressure extruded through a small opening and cut into larger particles which is subsequently dried. Extrusion is known from Michael S. Showell (editor); *Powdered detergents*; Surfactant Science Series; 1998; vol. 71; page 140–42; Marcel Dekker and U.S. Pat. No. 4,661, 452 both incorporated by reference.

Fluid Bed Processes

A fluid bed process in the context of the invention comprises fluidizing the spray dried enzyme containing particles in a fluid bed and atomizing a solution comprising a binder to the fluidized powder so as to bind the particles of the enzyme containing powder together to form larger and stronger particles.

The spray dried enzyme containing particles are less suitable use in processes for producing layered granules, herein defined as a process wherein the enzyme is applied as a layer around an inert particulate core material e.g. in a fluid bed device wherein the inert core is fluidized and the enzyme layer is applied by spraying onto the core an enzyme containing solution. Such a process requires re-dissolution or resuspension of the dried enzyme-containing powder in a liquid in order apply the enzyme containing layer around the inert core, thus introducing a more energy consuming step than for the processes, supra. Accordingly, in a preferred embodiment the subsequent processing of the dried enzyme containing particles is not a layering process.

Coating Processes

Spray dried particles or granules obtained there from may preferably be coated with one or more coating layers to provide further improved properties of the granule. Conventional coatings and methods as known to the art may suitably be used, such as the coatings described in WO 89/08694, WO 89/08695, 270 608 B1 and/or WO 00/01793. Other examples of conventional coating materials may be found in U.S. Pat. No. 4,106,991, EP 170360, EP 304332, EP 304331, EP 458849, EP 458845, WO 97/39116, WO 92/12645A, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A and/or JP 58179492.

The coating may comprise materials selected from binders, fibers, salts, water insoluble minerals, pigments, enzyme stabilizers or combinations thereof as described, supra, in the mixer granulation section.

In a particular embodiment the coating may comprise minor amounts of a protective agent capable of reacting with a component capable of inactivating (being hostile to) the enzyme entering the particle or granule from a surrounding matrix, i.e. before the component come into contact and inactivate the enzyme. The protective agent may thus e.g. be capable of neutralizing, reducing or otherwise reacting with the component rendering it harmless to the enzyme. Typical components capable of inactivating the enzyme are oxidants such as perborates, percarbonates, organic peracids and the like.

Protective agents may fall into several categories: alkaline or neutral materials, reducing agents, antioxidants and/or salts of first transition series metal ions. Each of these may be used in conjunction with other protective agents of the same or different categories. Examples of alkaline protective agents are alkali metal silicates, carbonates or bicarbonates which provide a chemical scavenging effect by actively neutralizing e.g. oxidants. Examples of reducing protective agents are salts of sulfite, thiosulfite or thiosulfate, while examples of antioxidants are methionine, butylated hydroxytoluene (BHT) or butylated hydroxyanisol (BHA). Most preferred agents are salts of thiosulfates, e.g. sodium thiosulfate. The amounts of protective agent in the coating may be 5–40% w/w of the coating, preferably 5–30%, e.g. 10–20%.

The coating should encapsulate the enzyme containing particle or granule by forming a substantially continuous homogenous layer.

The coating may perform any of a number of functions in the particle or granule, depending on the intended use. Thus, for example, a coating may achieve one or more of the following effects:

(i) further reduction of the dust-formation tendency of an enzyme particle or granule;
(ii) further protection of enzyme(s) in the enzyme particle/granule against oxidation by bleaching substances/systems (e.g. perborates, percarbonates, organic peracids and the like);
(iii) dissolution at a desired rate upon introduction of the particle/granule into a liquid medium (such as an aqueous medium);
(iv) provide a better physical strength of the enzyme particle/granule.

The coating may further comprise one or more of the following: anti-oxidants, chlorine scavengers, plasticizers, pigments, lubricants (such as surfactants or antistatic agents) additional enzymes and fragrances.

Plasticizers useful in coating layers in the context of the present invention include, for example: polyols such as sugars, sugar alcohols, or polyethylene glycols (PEGs) having a molecular weight less than 1000; urea, phthalate esters such as dibutyl or dimethyl phthalate; and water.

Suitable pigments include, but are not limited to, finely divided whiteners, such as titanium dioxide or kaolin, coloured pigments, water soluble colorants, as well as combinations of one or more pigments and water soluble colorants.

As used in the present context, the term "lubricant" refers to any agent which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents.

Examples of suitable lubricants are polyethylene glycols (PEGs) and ethoxylated fatty alcohols.

In a preferred embodiment of the invention the spray dried particle or subsequently processed granule of the invention is coated with a protective coating having a high constant humidity such as described in the Danish patent application WO 00/01793 pages 5–9, and given examples which was unpublished at the date of filing this application and which is hereby incorporated by reference.

Milling/grinding and Screening

It is to be understood that the processes as described above may suitably be supplemented with milling/grinding and/or screening processes at any stage of the processes. For example it may be desirable to grind the spray dried enzyme containing particles prior to subsequent processing steps and to screen the final product to obtain the a desired size fraction.

Particles Comprising Enzymes and Biomass

The invention encompasses particles comprising an enzyme and a biomass such as particles obtained by the second first aspect of the invention, i.e. particles obtained from a process selected from spray drying a fermentation broth, granulating a spray dried fermentation broth, coating a spray dried fermentation broth and granulating and coating a spray dried fermentation broth.

Applications

The particles of the invention is useful in a vide range of compositions and applications. Examples of useful compositions are cleaning compositions, textile processing compositions, leather processing compositions, pulp or paper processing compositions, food and beverage compositions, animal feed compositions and personal care compositions. Cleaning compositions includes such as detergents and anti-microbial compositions. Textile processing compositions includes compositions for enzymatic bleach and/or stone washing of textiles, such as denim. Food and beverage compositions includes enzymatic compositions used in industries producing wine, oils and fats, citrus and juice products, starch and sugar products, alcohols and/or brewed products, soy products and baking flour or dough.

Accordingly, the present invention encompasses compositions comprising particles comprising an enzyme and a biomass, preferably obtained from a process selected from spray drying a fermentation broth, granulating a spray dried fermentation broth, coating a spray dried fermentation broth and granulating and coating a spray dried fermentation broth.

The present invention also encompasses the use of particles comprising enzyme and biomass and compositions comprising such particles. Especially use for treatment of textile, leather, pulp, paper, food, beverage, hard surfaces and the human or animal body. The particles comprising enzyme and biomass and compositions comprising such particles may also be used in the manufacture of a medicament for treatment of the human or animal body.

Detergent Compositions

A preferred composition is a detergent composition comprising a surfactant and an enzyme and biomass containing particle obtained from spray drying a fermentation broth or a granule obtained from such spray dried particle.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme and biomass containing spray dried particle or granule of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, is formulated so as to contain one or more of the enzyme granules of the invention.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides")

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), polylvinyl alcohol), poly(vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liqour, preferably 0.05–5 mg of enzyme protein per liter of wash liqour, in particular 0.1–1 mg of enzyme protein per liter of wash liqour.

The enzyme of the invention may additionally be incorporated in the detergent formulations disclosed in WO 97/07202 which is hereby incorporated as reference.

Materials and Methods

The unit for protease activity used herein is Kilo Novo Protease. KNPU of a sample is determined relatively to a Savinase® standard in a standard assay by measuring for a given amount of sample the formation rate ($\mu$mol/minute) of free amino groups liberated from digestion of di-methylcasein (DMC) in solution by the enzyme in the sample. The formation rate is monitored by recording the linear development of absorbance at 420 nm of the simultaneous reaction between the formed free amino groups and added 2,4,6-tri-nitro-benzene-sulfonic acid (TNBS). The digestion of DMC and the colour reaction is carried out at 50° C. in a pH 8.3 boric acid buffer with a 9 min. reaction time followed by a 3 min. measuring time.

EXAMPLE 1

Spray-drying of a high product titre protease fermentation broth.

A production size batch of protease containing fermentation broth with an dry matter content of 13% w/w was sieved through a rotary brush strainer to remove large solid particulates. The fermented micro-organism was killed by adding 0.5% Rodalon (50% Senzalkoniumchlorid) to the broth while maintaining agitation. Formic acid was then added to reduce pH to 5.5 and the broth left for an hour or more to allow the Rodalon to be effective. The broth was heated to an inlet temperature of 140° C. and introduced to a drying chamber (Niro Atomizer, SD200-R spray drying tower) via a rotating spray nozzle. The exit temperature being 55° C. The resulting spray dried powder had an activity of 41 KNPU/g and a water content of 4.86%.

EXAMPLE 2

Production-scale spray-drying of a high product titre cellulase fermentation broth.

A production size batch of cellulase containing fermentation broth is sieved through a rotary brush strainer to remove large solid particulates. To kill the production strain, 0.5% Rodalon Oil is (50% Benzalkoniumchlorid) is added while the broth is well agitated and the broth is left for at least one hour to allow the Rodalon to be effective. The broth introduced to a spray tower (Niro Atomizer, SD-200-R) via a rotating spray nozzle at an inlet temperature of 140° C. The exit temperature should be around 55° C. The resulting spray dried powder have an estimated activity of 20000 ECU/g and a water content estimated below 5.0% w/w.

EXAMPLE 3

Production-scale spray-drying of a high product titre amylase fermentation broth.

A production size batch of amylase containing fermentation broth is sieved through a rotary brush strainer to remove large solid particulates. To kill the production strain, 0.5% Rodalon (50% Benzalkonium-chlorid) is added while the broth is well agitated and the broth is left for at least one hour to allow the Rodalon to be effective. The broth is introduced to the spray tower (Niro Atomizer, SD-200-R) via a rotating spray nozzle at an inlet temperature of 140° C. The exit temperature should be around 55° C. The resulting spray dried powder have an estimate activity of 960 KNU/g and a water content estimated below 5.0% w/w.

What is claimed is:

1. A process for preparing enzyme containing particles, said process comprising spray drying a fermentation broth comprising an enzyme and a biomass, to obtain solid particles comprising an enzyme and a biomass having a mean particle size of about 50–300μ and a SPAN value below about 2.5.

2. The process of claim 1, wherein the fermented micoorganism in the biomass is a strain selected from *Bacillus, Candida, Hansenuls, Kluyveromyces, Pichia, Sacchammyces, Schizosaccharomyces, Yarrowia, Acremonium, Aspergillus, Fusarium, Humicola, Mucor, Myceliophthora, Neurospora, Penicillium, Thielavia, Tolypocladium*, and *Trichoderma*.

3. The process of claim 1, wherein the enzyme is selected from oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

4. The process of claim 1, wherein the biomass in the solid particle constitutes at least 10% of the biomass originating from the fermentation broth.

5. The process of claim 4, wherein the biomass in the solid particle constitutes at least 50% of the biomass originating from the fermentation broth.

6. The process of claim 5, wherein the biomass in the solid particle constitutes at least 75% of the biomass originating from the fermentation broth.

7. The process of claim 6, wherein the biomass in the solid particle constitutes at least 90% of the biomass originating from the fermentation broth.

8. The process of claim 1, wherein the fermentation broth contains 0–30% w/w dry matter.

9. The process of claim 1, further comprising de-sludging of the fermentation broth before spray drying.

10. The process of claim 1, wherein additives selected from inorganic salts, inorganic minerals or clays, carbohydrates, coloring pigments, cellulose or derivatives thereof, biocides, dispersants, anti-foaming agents, viscosity regulating agents, acid agents, alkaline agents, enzyme stabilizers, enzyme inhibitors, binders, other enzymes and combinations thereof have been added to the fermentation broth prior to spray drying.

11. The process of claim 1, wherein the fermentation broth has been subjected to a physical treatment prior to spray drying selected from heating, cooling, radiating, mixing, aerating and ultra-sound treatment.

12. The process of claim 1, wherein the fermentation broth has been sterilized.

13. The process of claim 1, wherein the fermentation broth has been treated to hydrolyse polynucleotides.

14. The process of claim 1, wherein the fermentation broth contains at least 3 mg active enzyme protein per liter in the liquid phase.

15. The process of claim 1, wherein the fermentation broth has a viscosity of 5–5000 cps.

16. The process of claim 1, further comprising the step of additional drying of the spray dried particles in a fluid bed dryer.

* * * * *